US007008425B2

(12) United States Patent
Phillips

(10) Patent No.: US 7,008,425 B2
(45) Date of Patent: Mar. 7, 2006

(54) PEDIATRIC INTRAMEDULLARY NAIL AND METHOD

(76) Inventor: Jonathan Phillips, 3527 Bellington Dr., Orlando, FL (US) 32835

( * ) Notice: Subject to any disclaimer, the term of this patent is extended or adjusted under 35 U.S.C. 154(b) by 271 days.

(21) Appl. No.: 09/990,243

(22) Filed: Nov. 21, 2001

(65) Prior Publication Data

US 2002/0111629 A1    Aug. 15, 2002

Related U.S. Application Data

(63) Continuation-in-part of application No. PCT/US00/14840, filed on May 26, 2000, which is a continuation-in-part of application No. 09/321,369, filed on May 27, 1999, now abandoned.

(60) Provisional application No. 60/252,536, filed on Nov. 22, 2000.

(51) Int. Cl.
*A61B 17/56* (2006.01)
(52) U.S. Cl. ............................................ 606/62; 606/67
(58) Field of Classification Search .................. 606/62, 606/59, 60, 61, 63, 65, 66, 67, 68, 72, 73
See application file for complete search history.

(56) References Cited

U.S. PATENT DOCUMENTS

| 3,760,802 A |   | 9/1973  | Fischer et al. |
|---|---|---|---|
| 4,483,335 A |   | 11/1984 | Tornier |
| 4,503,847 A |   | 3/1985  | Mouradian |
| 4,667,664 A |   | 5/1987  | Taylor et al. |
| 4,712,541 A |   | 12/1987 | Harder et al. |
| 4,781,181 A |   | 11/1988 | Tanguy |
| 4,788,847 A | * | 12/1988 | Sterghos ...................... 72/213 |
| 4,827,917 A |   | 5/1989  | Brumfield |
| 4,832,883 A | * | 5/1989  | Kato et al. .................. 264/40.1 |
| 4,862,883 A | * | 9/1989  | Freeland ....................... 606/64 |
| 4,913,137 A | * | 4/1990  | Azer et al. ..................... 606/64 |
| 4,915,092 A |   | 4/1990  | Firica et al. |
| 5,019,079 A |   | 5/1991  | Ross |
| 5,034,013 A | * | 7/1991  | Kyle et al. .................... 606/62 |
| 5,035,697 A | * | 7/1991  | Frigg .......................... 606/67 |
| 5,041,115 A | * | 8/1991  | Frigg et al. ................... 606/62 |
| 5,053,035 A |   | 10/1991 | McLaren |
| 5,084,053 A |   | 1/1992  | Ender |
| 5,248,313 A |   | 9/1993  | Greene et al. |
| 5,354,305 A | * | 10/1994 | Lewis, Jr. et al. .......... 606/152 |
| 5,569,249 A |   | 10/1996 | James et al. |
| 5,620,449 A | * | 4/1997  | Faccioli et al. ............... 606/98 |

(Continued)

FOREIGN PATENT DOCUMENTS

WO    WO 00/72767 A1    7/2000

*Primary Examiner*—Pedro Philogene
(74) *Attorney, Agent, or Firm*—Krieg DeVault LLP

(57) ABSTRACT

An intramedullary nail (20) and related method for fixing a fracture in a long bone. The nail (20) comprises an elongate member (22) having a longitudinal axis (54), a proximal end section (32), a distal end section (34) and a solid central section (24) extending between the proximal and distal end sections (32, 34). The proximal and distal end sections (32, 34) respectively include proximal and distal fastener receiving areas (28, 30) of greater cross sectional dimensions than the central section (24). Each fastener receiving area (28, 30) includes at least one hole (50, 52) extending transverse to the longitudinal axis for receiving a cross fastener (110) adapted to secure to the bone on opposite sides of the elongate member (22). The proximal and distal end sections (32, 34) thereby provide rigid anchoring locations relative to the central section (24) and the central section provides flexibility to promote healing of the fracture.

15 Claims, 10 Drawing Sheets

U.S. PATENT DOCUMENTS

| | | |
|---|---|---|
| 5,855,579 A | 1/1999 | James et al. |
| 5,879,352 A | 3/1999 | Filoso et al. |
| 5,928,235 A | 7/1999 | Friedl |
| 6,010,506 A * | 1/2000 | Gosney et al. ............... 606/62 |

* cited by examiner

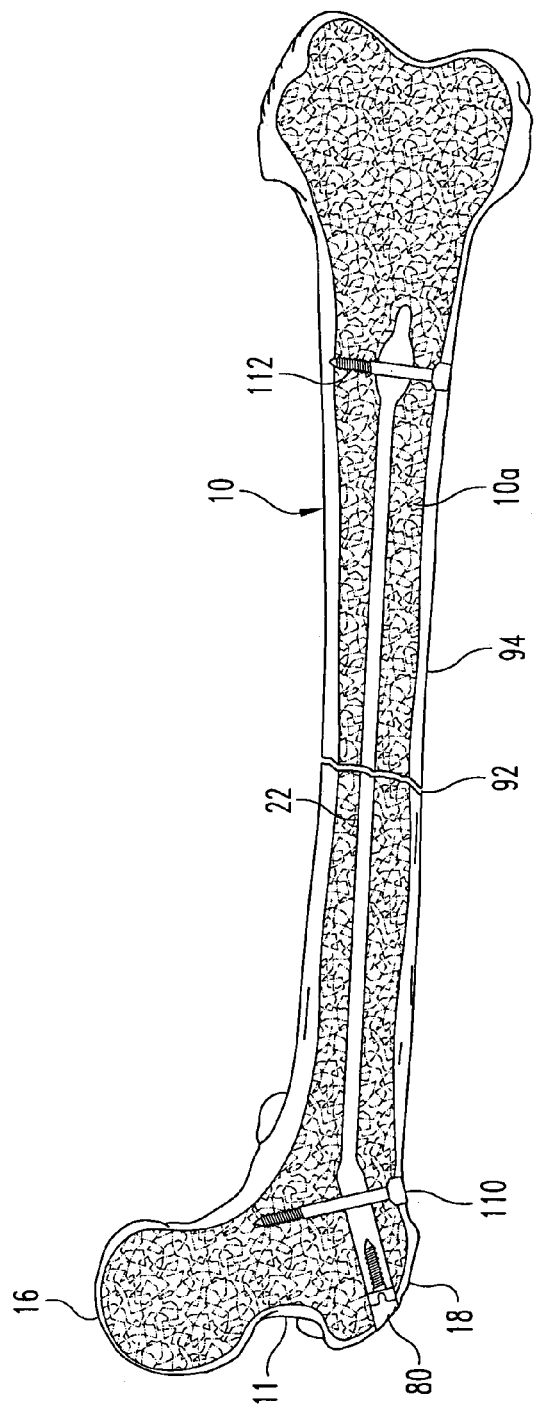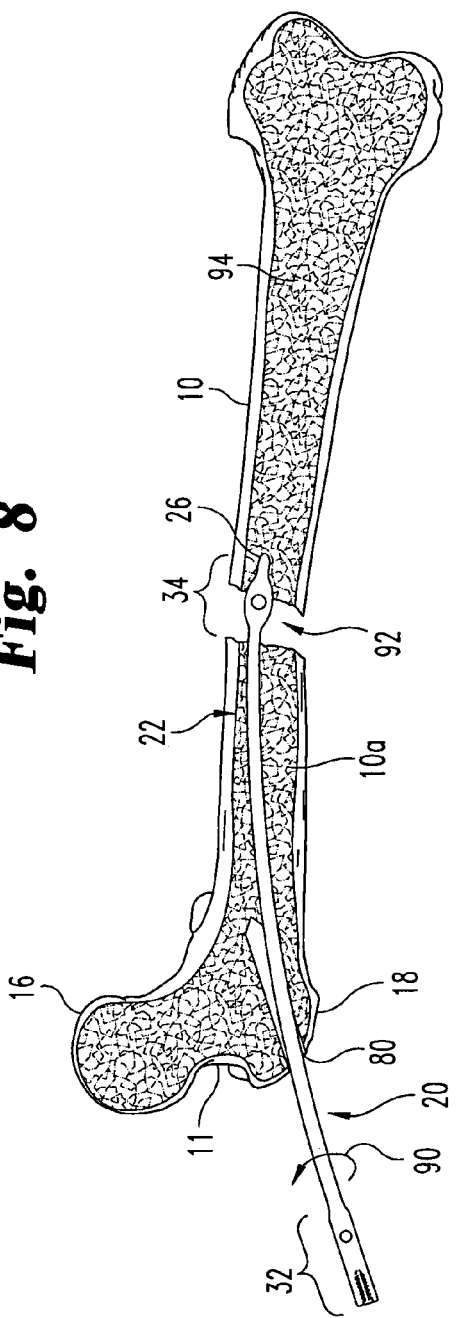

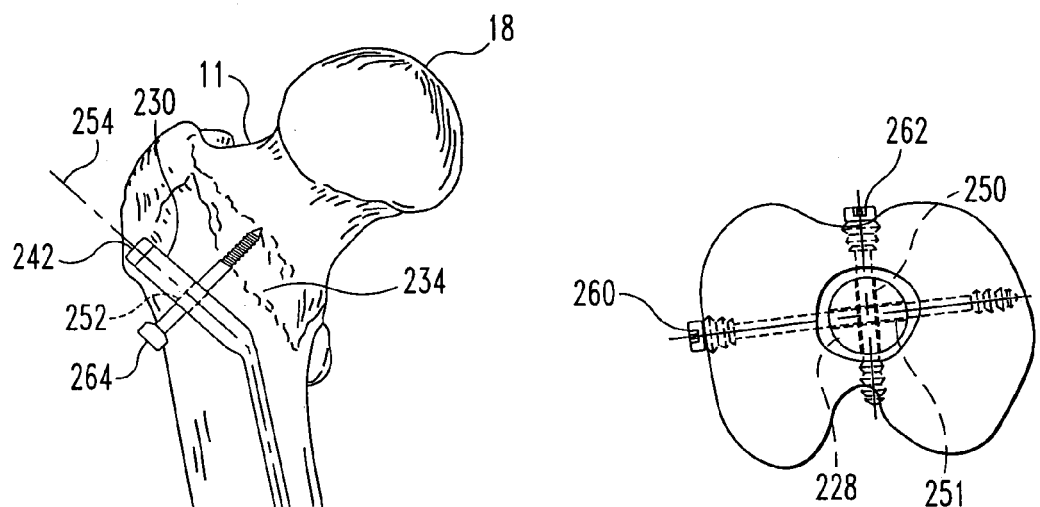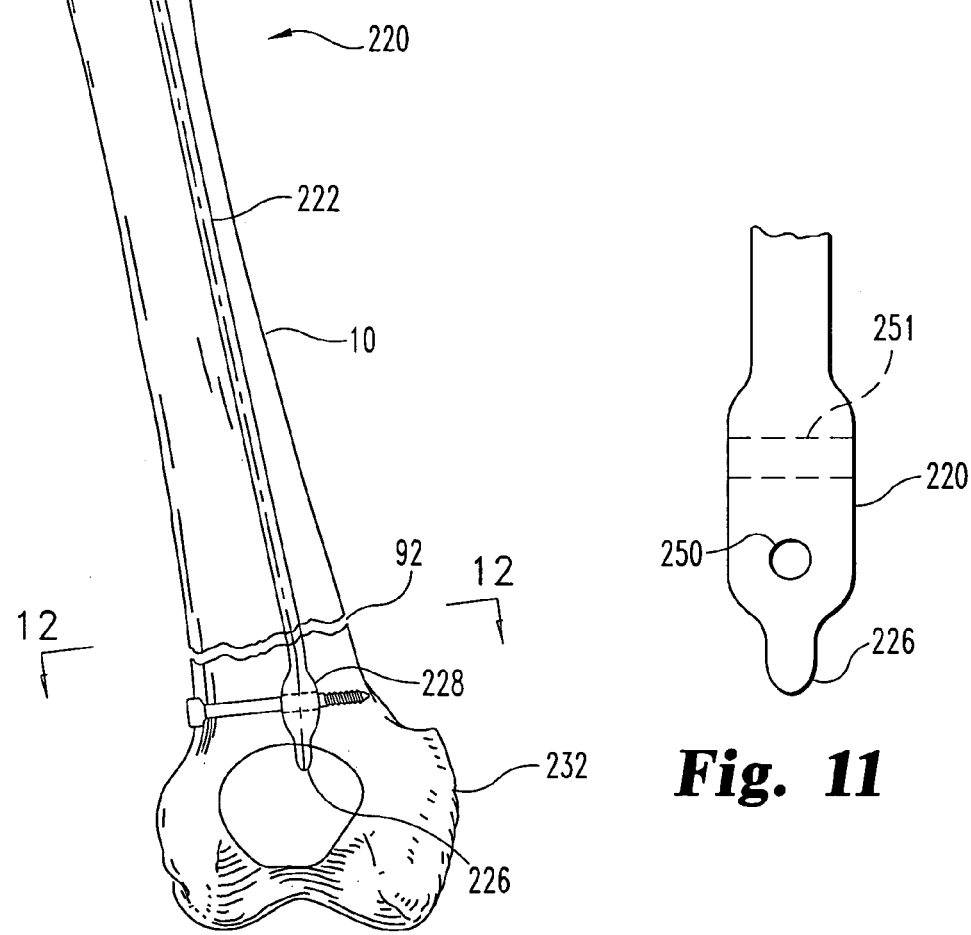
Fig. 10
Fig. 11
Fig. 12

PEDIATRIC INTRAMEDULLARY NAIL AND METHOD

CROSS-REFERENCE TO RELATED APPLICATIONS

The present application claims the benefit of U.S. Provisional Patent Application No. 60/252,536 filed 22 Nov. 2000, the disclosure of which is entirely incorporated by reference herein, and which is a continuation-in-part of International Patent Application No. PCT/US00/14840 filed 26 May 2000 and published in the English language 7 Dec. 2000, the disclosure of which is entirely incorporated by reference herein, and which is a continuation in part of U.S. patent application Ser. No. 09/321,369 filed 27 May 1999, now abandoned the disclosure of which is entirely incorporated by reference herein.

BACKGROUND OF THE INVENTION

1. Field of the Invention

The present invention relates to devices and methods for repairing bone fractures, and, more particularly, to intramedullary nails and related internal fixation methods especially suitable for repairing long-bone fractures in children.

2. Description of Related Art

The use of intramedullary nails in the repair of long-bone fractures, such as in the femur, has been known in the orthopedic field. Exemplary devices include those known as the Rush and Enders and the Kuntschner nails, as well as those disclosed in U.S. Pat. No. 5,713,902 to Friedl; U.S. Pat. No. 5,697,930 to Itoman et al.; U.S. Pat. No. 5,573,536 to Grosse et al.; U.S. Pat. No. 5,562,666 to Brumfield; U.S. Pat. No. 5,374,235 to Ahrens; U.S. Pat. Nos. 5,312,406 and 5,167,663 to Brumfield; U.S. Pat. No. 5,122,141 to Simpson; U.S. Pat. Nos. 5,066,296, 5,041,114, and 4,776,330 to Chapman et al.; U.S. Pat. No. 4,976,258 to Richter et al.; U.S. Pat. No. 4,875,475 to Comte et al.; U.S. Pat. No. 4,846,162 to Moehring; U.S. Pat. No. 4,506,662 to Anapliotis; and U.S. Pat. No. 4,475,545 to Ender.

Referring to FIG. 1, a special problem in pediatric orthopedics exists in that reaming through the typical entry point in a femur 10, i.e., the piriformis fossa 11, can be to dangerous for the child. This is due to the presence of an artery 12 that supplies blood to the proximal femur. Specifically, this is the lateral epiphyseal artery 12 which is a branch of the femoral artery. If this artery 12 is damaged during the fixation procedure, such as while the intramedullary canal is being reamed to accept a nail, or possibly during insertion or after insertion of the nail, various complications can result. The lateral epiphyseal artery 12 supplies 75% of the blood to the growing femoral head 16. If this artery 12 is damaged, then much of the femoral head 16 will die or necrose. The femoral head 16 will then heal with an irregular shape which inevitably leads to hip arthritis. Various nails, such as flexible Rush nails, are non-interlocked meaning that cross fasteners are not used to secure the nail to the bone. These nails are often small diameter rods, on the order of approximately 3–4 mm in diameter. In addition to being flexible to a significant degree prior to plastic deformation, non-interlocked solid nails or rods can be relatively easily bent with plastic deformation to a desired shape. A plurality of these nails or rods are typically driven into the intramedullary canal depending on the support necessitated by the fracture and bone characteristics of the patient. Other more rigid solid or hollow nails are interlocked to the bone using cross fasteners typically at the proximal and distal ends of the nail. Unlike non-interlocked nails, interlocked nails require sufficient cross-sectional dimensions to accommodate holes necessary for the cross fasteners. Currently available interlocked nails can be inserted away from the lateral epiphyseal artery 12 but are so rigid that they migrate during insertion dangerously close to the artery 12 and can endanger it. In addition, the large proximal size of small adult interlocked nails, which have typically been used in children, increases the potential for damage to the growth plate 17 at the proximal femur.

Among possible solutions, retrograde nailing avoids the proximal femur but also has at least one potential problem. The nails must be introduced close to the distal femoral growth plate or physis 19 (FIG. 5) at an awkward angle, potentially causing growth arrest distally on the femur, i.e., adjacent the knee. An approach through the greater trochanter 18 is also well recognized, but usually only one small diameter non-interlocked nail or rod can be used because of the narrow safe entry zone of the greater trochanter. A second small diameter nail or rod needs to be inserted retrograde or through the opposite end of the femur in these situations. These small diameter, flexible nails allow flexure after insertion and the slightly added stress to the bone allowed by this flexure promotes faster bone healing. These non-interlocked nails work well for transverse fractures. However, spiral or comminuted fractures often need additional external support, such as with a cast or brace. This is due to the inability of the non-interlocked nail to effectively, prevent rotation or length compromise at the fracture.

It would therefore be desirable to provide an interlocked intramedullary nail, especially suitable for pediatric use, which provides flexibility along a majority of the length of the nail to facilitate faster healing of a fracture, but which also provides for secure interlocking of the nail to the bone with cross fasteners to prevent compromising the fracture due to rotation or shortening at the fracture site. Ideally, such a nail and related methods of insertion would minimize trauma to the growth plates of the femur as well as the arteries that supply blood to the proximal end of the femur while still allowing easy insertion and fixation within the intramedullary canal.

SUMMARY OF THE INVENTION

In one general aspect, the present invention provides an intramedullary nail for insertion within an intramedullary canal of a long bone and fixing a fracture in the long bone. The nail is especially suitable for adolescent or preadolescent aged children, however, the nail may be useful in other orthopedic applications as well. The nail generally comprises an elongate member having a longitudinal axis, a proximal end section, a distal end section and a solid central section extending between the proximal and distal end sections. The proximal and distal end sections respectively have fastener receiving areas of greater cross sectional dimensions than the central section. The fastener receiving areas each include at least one hole extending transverse to the longitudinal axis of the elongate member for receiving a cross fastener adapted to secure to the bone on opposite sides of the elongate member. The proximal and distal end sections provide rigid anchoring locations relative to the central section and the central section provides flexibility to promote healing of the fracture.

In the preferred embodiment, the central section of the elongate member is curved in the sagital plane to generally follow the curvature of a femur. The proximal and distal end sections are bent out of this plane and form acute angles with respect to the sagital plane. The proximal and distal end sections are each bent laterally to one side of the central section. The side to which the proximal and distal end sections are bent depends on whether the nail will be used in a right or left femur and also allows easier insertions across the fracture. The bend of the distal end section allows for easier insertion of the nail from an insertion point extending through the greater trochanter of the femur. The bend of the proximal end section ensures that the proximal tip is presented directly at the insertion point after fixation so that it may be easily accessed for removal purposes upon healing of the bone.

In general, a method of fixing a fracture in a long bone of a patient, in accordance with the invention, includes providing an elongate member having a solid central section with a cross sectional dimension and having proximal and distal fastener receiving areas of increased cross sectional dimension relative to the cross sectional dimension of the central section. The fastener receiving areas each have at least one hole extending transverse to a longitudinal axis of the elongate member. The method involves inserting the elongate member into the intramedullary canal of the long bone through an insertion point and across the fracture and inserting cross fasteners through each of the holes and into the bone on opposite sides of the elongate member to fix the fracture of the long bone against rotational and lengthwise movements.

The bone nail and method of this invention allow the surgeon to better avoid the critical arterial blood supply to the femoral head which crosses at the piriformis fossa, i.e., the traditional point of entry for an adult nail. Instead the entry point is on the greater trochanter, a location distinctly lateral of the critical region of the piriformis fossa. The very vulnerable growth plate between the greater trochanter and the femoral neck is also avoided using the nail and entry point in accordance with this invention. Another unique feature of the invention is the ability of the bone nail to be flexible, yet custom bent to match the exact geometry of the proximal femur, while also allowing interlocking with cross fasteners. In general, the preferred inventive nail provides interlockability, a relatively small solid cross section to provide flexure along at least the majority of the length of the nail, and malleability to allow custom bending especially at the proximal end.

The features that characterize the invention, both as to organization and method of operation, together with further objects, features and advantages thereof, will be better understood from the following written description taken in conjunction with the accompanying drawings. It is to be expressly understood that the drawings and detailed description thereof are for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

FIG. 6 is a schematic view similar to FIG. 5, but illustrating the nail further inserted across the bone fracture.

FIG. 8 is a schematic illustration of the fully inserted and cross fastened bone nail.

FIG. 10 is an elevational schematic view of another embodiment bone nail according to the present invention fully inserted in the femur.

FIG. 11 is an enlarged view of the distal end portion of the nail of FIG. 10.

FIG. 12 is a sectional view taken through line 12—12 of FIG. 10.

DETAILED DESCRIPTION

Figure 1:
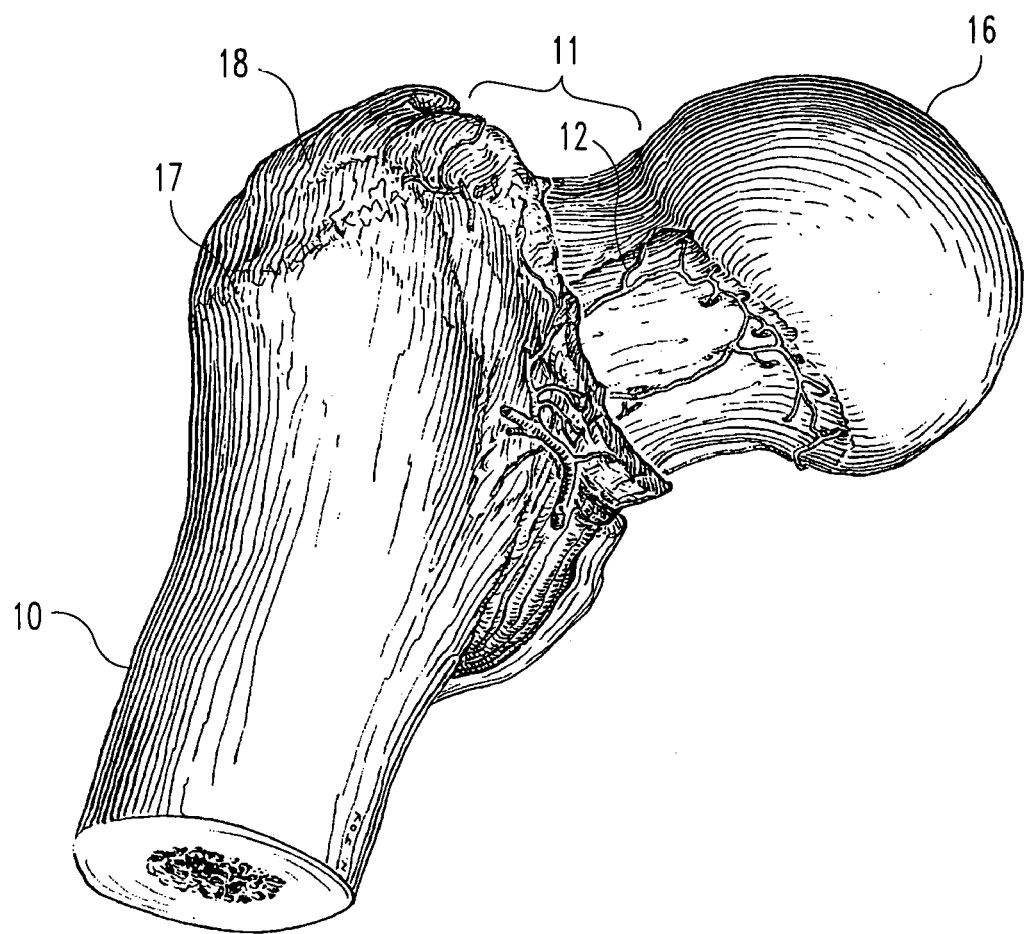
FIG. 1 is a perspective view of a portion of a femur including the femoral head and the greater and lesser trocantic regions.
Figure 2:
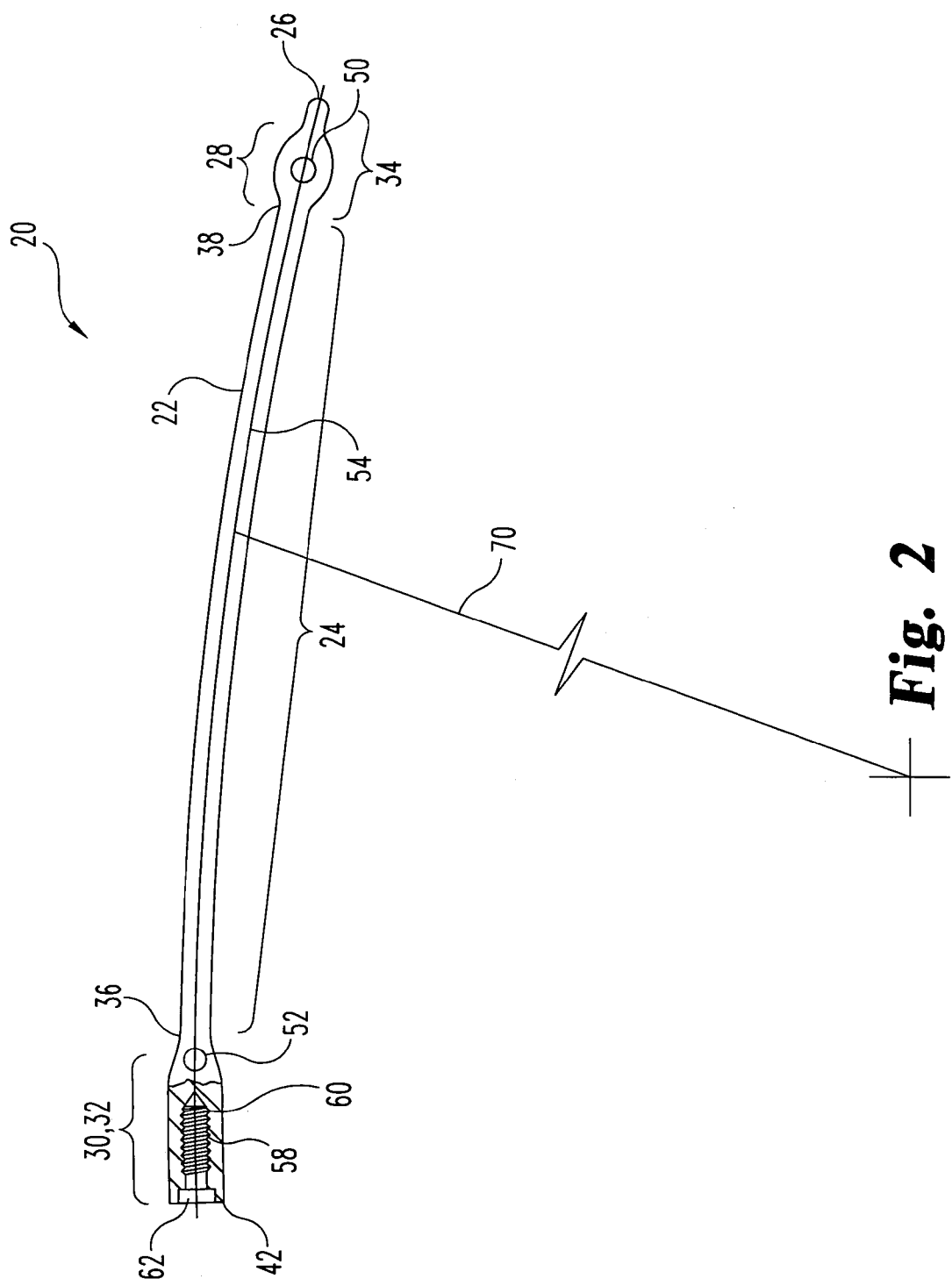
FIG. 2 is a side elevational view of an intramedullary nail of the present invention shown in the anterior-posterior plane.
Figure 3:
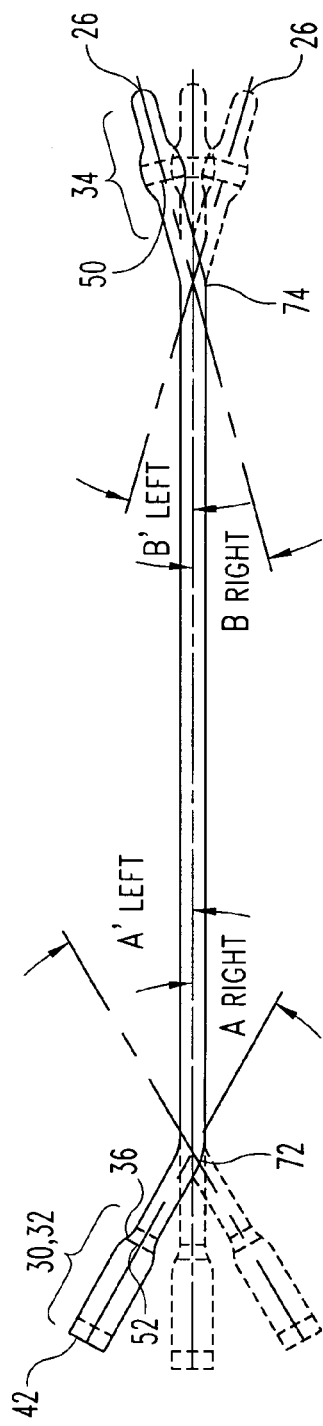
FIG. 3 is an elevational view of the nail shown in FIG. 2, but illustrating proximal and distal bends.
Figure 4:
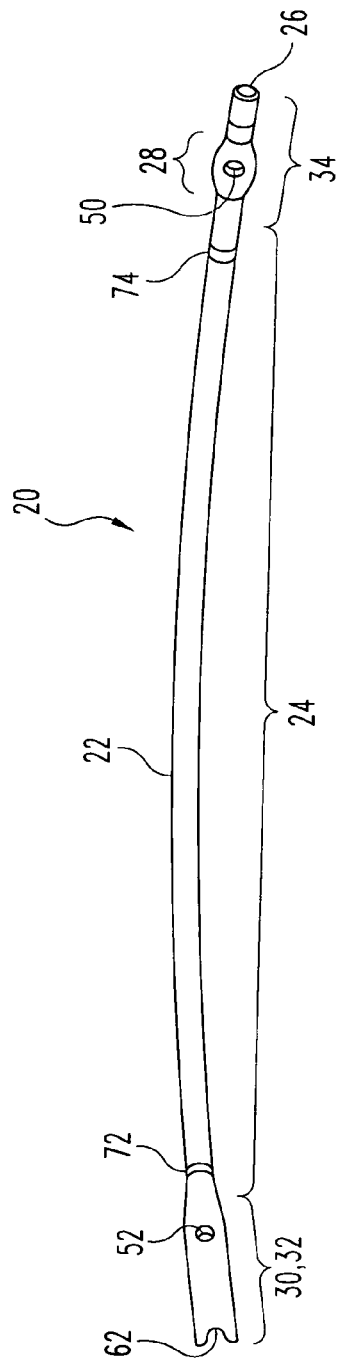
FIG. 4 is an elevational view of the nail shown in FIG. 3, but rotated 90°.
Figure 5:
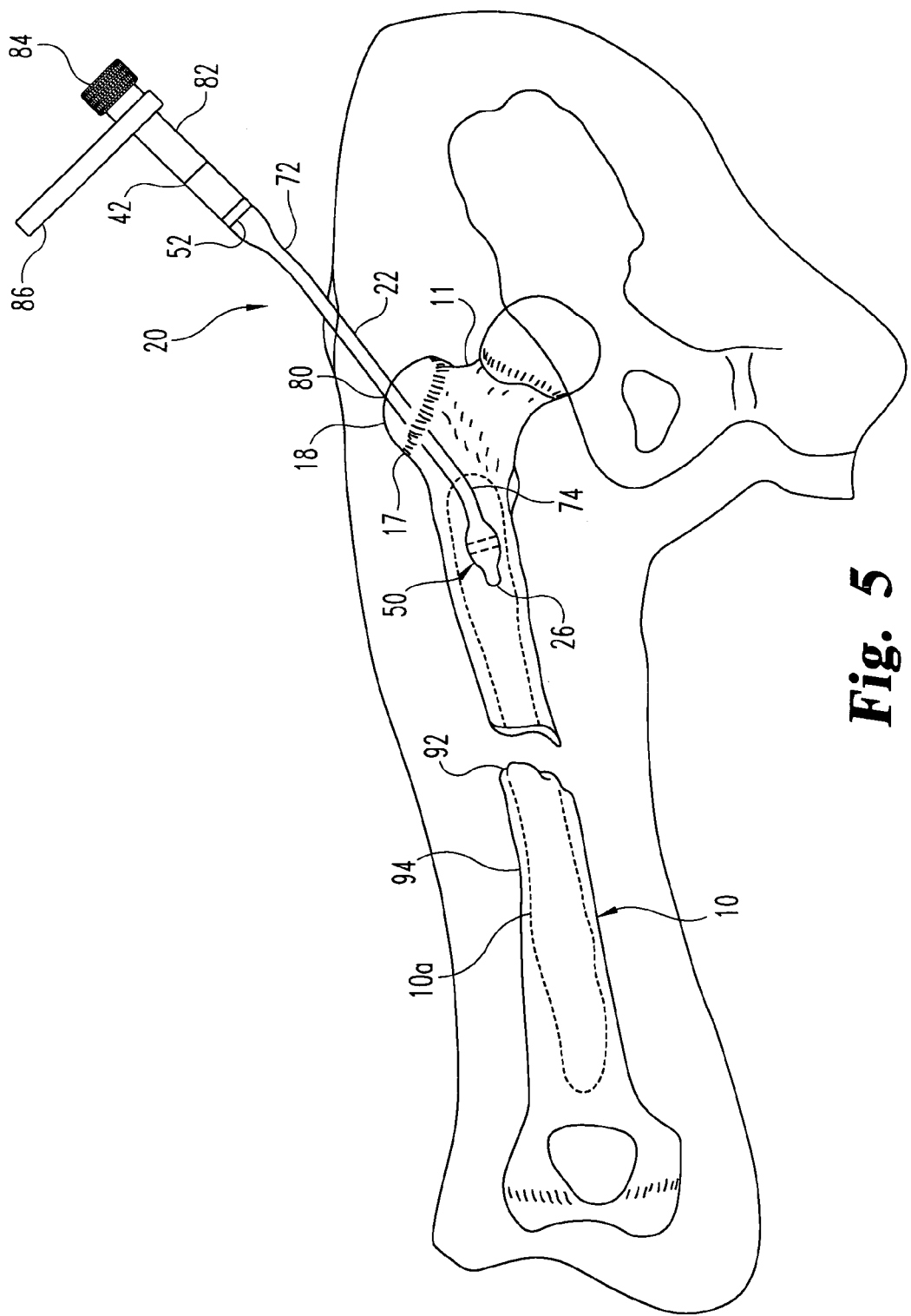
FIG. 5 is a schematic view of the step of initially inserting the bone nail of FIGS. 3 and 4 into a femur.

An exemplary intramedullary nail 20, as illustrated in FIGS. 2–4, comprises an elongate member 22. In an embodiment intended for use in a femur of a child or adolescent, typically ages 6–14, for example, the nail 20 is formed from titanium and has a generally cylindrical shape with a diameter along a solid central section 24 of between 4 mm and 7 mm, although this is not intended as a limitation. Central section 24 should have a certain amount of elastic flexibility to permit accurate placement within the femoral canal as discussed below. Such elastic flexibility, which permits some flexure during movement and weight bearing activity, confers an additional benefit in that it has been found to stimulate bone healing. The nail 20 preferably ends in a rounded, smooth and tapered distal tip 26.

The nail 20 has two widened sections or fastener receiving areas 28, 30 in respective proximal and distal end sections 32, 34. Each fastener receiving area 28, 30 is formed with an increased cross sectional dimension relative to central section 24. Also, smooth, gradual transitions 36, 38 with the central section 24 avoid sharp edges along the length of nail 20. The distal fastener receiving area 28 is positioned adjacent to but in spaced relation from distal tip 26. The distal fastener receiving area 28 tapers on both proximal and distal sides thereof. The proximal fastener receiving area 30 extends to proximal tip 42; that is, there is a distal taper but no proximal taper, and the widened proximal fastener receiving area 30 instead continues to the proximal tip 42 and forms the entire proximal end section 32.

Each fastener receiving area 28, 30 includes a generally cylindrical hole 50, 52 extending generally normal to the portion of the longitudinal axis 54 in which it is located for receiving a fastener (not shown). Holes 50, 52 preferably have diameters in a range of 3 mm to 4½ mm.

Proximal tip 42 includes attachment structure 58 for receiving a driver, described below, which may be a conventional driver used in the bone nail art. Preferably, attachment structure 58 comprises a threaded axial bore 60 extending along axis 54 and engageable with an externally threaded driver. A notch 62 extends across bore 60 and, as is known, aligns the driver for purposes of later drilling and cross fastening nail 20, as will be discussed below. As further shown in FIGS. 2 and 4, nail 20 is curved in an anterior direction along a radius of curvature 70 to generally conform nail 20 to the typical femoral curvature. Preferably, this radius of curvature 70 is in the range of 30 inches to 60 inches. A proximal bend 72 and a distal bend 74 are formed, respectively, in central section 24 directly adjacent proximal and distal end sections 32, 34. These bends 72, 74 are made in the same direction, i.e., laterally to one side of nail 20 or the other as shown best in FIG. 3. The solid lines in FIG. 3 illustrate lateral bends 72, 74 out of the sagital plane and generally in the coronal plane at angles A, B for inserting nail 20 into a left femur. Angles A', B' corresponding to the respective lateral bends of proximal and distal end sections 32, 34, shown in phantom, facilitate use of nail 20 in the right femur. As a unique feature of this invention, interlocking nail 20 may be custom bent by the surgeon just prior to use, not only to facilitate insertion in the right or left femur, but also to accommodate other particular shapes necessary for a particular patient. For example, some patients may have deformities necessitating one or more corrective osteotomies or fractures made by the surgeon. These osteotomies may also be fixed using nail 20.

In the preferred embodiment, nail 20 is formed from titanium, although other materials such as those known in the art may be used as well. Central section 24 is of solid cross section and at least substantially constant diameter with a smooth outer surface to facilitate removal in 6–9 months. Proximal and distal end sections 32, 34 are also solid, except for holes 50, 52, bore 60 and notch 62. As appreciated from FIG. 2, the axes of holes 50, 52 are coplanar. In order to provide the desired flexibility of central section 24, while retaining the cross fastening feature of the invention, fastener receiving areas 28, 30 have a cross sectional dimension greater than the cross sectional dimension of central section 24. In general, central section 24 may be formed with a solid cylindrical cross section having a diameter of between 4 mm and 7 mm. Fastener receiving area 28 has a generally bulbous, rounded shape, while proximal fastener receiving area 30, which is preferably continuous with distal end section 32, has a cylindrical cross sectional shape. At the cross section taken along the axes of respective holes 50, 52, the respective ratios of the cross sectional dimensions at these locations is at least about 1.3:1 relative to the cross sectional dimension of central section 24. In exemplary embodiments of the invention, a nail 20 substantially as shown in FIG. 2, had a cross sectional dimension of 5.5 mm for central section 24, an 8.5 mm cross sectional dimension for proximal end section 32, and also a maximum 8.5 mm cross sectional dimension at the largest diameter portion of distal fastener receiving area 28. This nail was used on children generally weighing less than 100 lbs. For children weighing more than 100 lbs., the 8.5 mm dimensions at the proximal and distal fastener receiving areas remained the same, while the cross sectional dimension for central section 24 was increased slightly to 6.5 mm to provide additional strength but still provide the desirable flexure.

Figure 7:
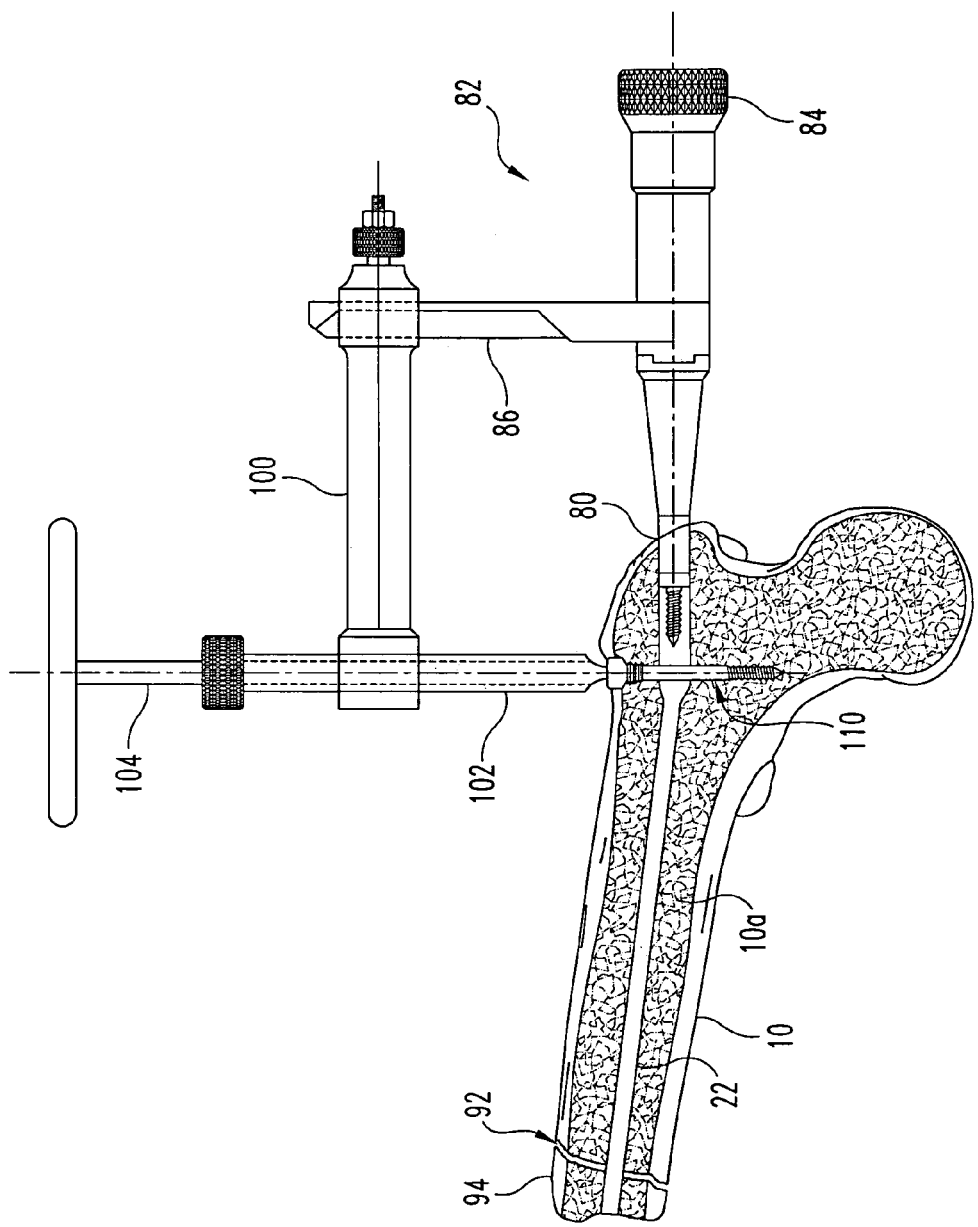
FIG. 7 illustrates a drill rig and fastener inserting rig being used to cross fastened the nail after full insertion.
Figure 8A:
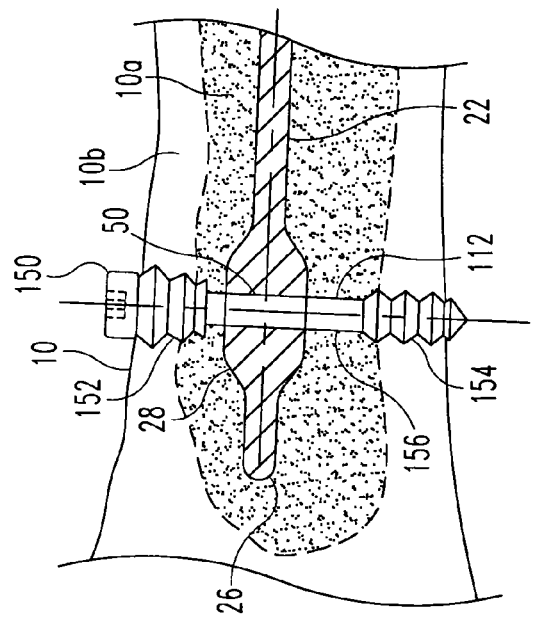
FIG. 8A is a fragmented, partially sectioned view of the distal end section of the bone nail and the cross fastener of the present invention.

The insertion and fixation techniques according to the preferred embodiment of the invention are best illustrated in FIGS. 5–8. In accordance with the invention, an insertion point 80 is created in the greater trochanter 18 of the femur 10 of a child, for example, at a distinctly lateral position relative to the piriformis fossa 11. Intramedullary canal 10*a* of femur 10 is drilled and reamed in a known manner to accept bone nail 20. A driver 82 is coupled with proximal tip 42, also in a known manner, and the surgeon impacts the head 84 of the driver 82 while holding the handle portion 86. Bend 74 facilitates better positioning of distal tip 26 upon insertion of nail 20 by allowing distal tip 26 to naturally follow the intramedullary canal 10*a* relative to the angle of the insertion point 80 in the greater trochanter 18. As shown in FIG. 6, bone nail 20 may be rotated in either direction represented by arrow 90 as the distal tip 26 approaches and crosses the fracture 92. This allows the surgeon, using fluoroscopy, to more easily locate and enter the intramedullary canal 10*a* of the distal bone segment 94. After the bone nail 20 is fully inserted, as shown in FIG. 7, a drill rig 100 is attached to the proximal tip 42 through securement to handle portion 86. The drill rig 100 aligns a drill guide 102 with the proximal fastener receiving hole 52 and a drill (not shown) is used to form a hole through femur 10 in line with hole 52. A screw driving mechanism 104 is then used to insert a cross fastener 110 at this location. Using conventional fluoroscopy techniques, a second hole is drilled and a second cross fastener 112, preferably of the same design as fastener 110, is inserted through the distal hole 50, as shown in FIGS. 8 and 8A. More specifically, and as represented by distal fastener 112 in FIG. 8A, fastener 112 comprises a drive head 150, a proximal threaded portion 152, a distal threaded portion 154, and a central unthreaded portion 156 which is received within hole 50. Threaded portions 152, 154 are securely engaged within cortical layer 10*b* of femur 10. In this manner, bone nail 20 is interlocked to femur 10 at proximal and distal locations thereby preventing undesirable rotational and/or lengthwise bone movements at the fracture site. In this interlocked or fixed position, proximal tip 42 is presented directly at the insertion point 80 on the greater trochanter 18 so that, upon healing of the fracture, the cross fasteners 110, 112 may be removed and threaded bore 60 may be engaged to withdraw nail 20 from intramedullary canal 10*a*.

Figure 9:
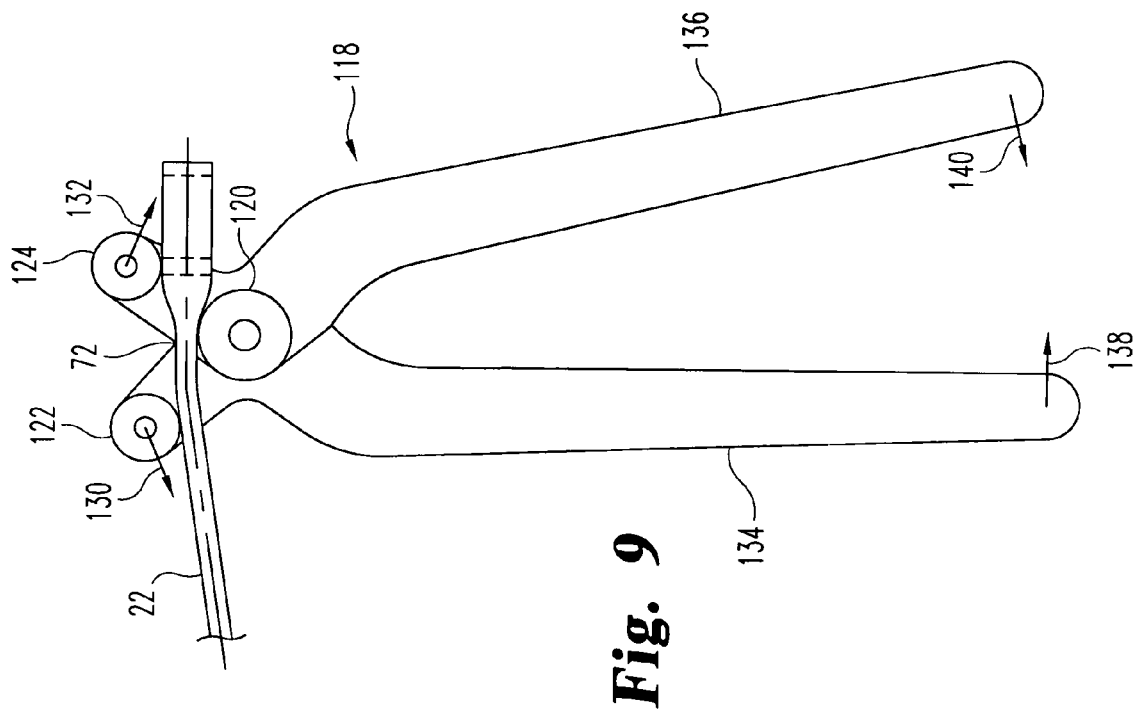
FIG. 9 is an elevational view showing one illustrative bending device being used to bend the proximal end section of the bone nail.

Although bends 72, 74 may be pre-made by a manufacturer of nail 20, for example, the present invention further contemplates a manual bending device as shown in FIG. 9. Using this device, nail 20 may be placed by the surgeon in a bending device 118 jaw structure comprising three rollers 120, 122, 124 with one roller 120 acting as a fulcrum and two opposite rollers 122, 124 applying forces in the direction of arrows 130, 132. When the handles 134, 136 of the device are squeezed together in the direction of arrows 138, 140, proximal end section 32 will be bent relative to central section 24 to form bend 72 as best illustrated in FIG. 3 and as previously described. The same procedure may be used by the surgeon to bend distal end section 34 just prior to insertion within intramedullary canal 10*a*. This aspect of the invention allows the surgeon to custom bend these or other portions of the nail 20 to suit the anatomy and/or needs of a particular patient prior to or during surgery.

Other embodiments for an intramedullary nail for insertion in an intramedullary canal to repair fractures or osteotomies of a long bone are also contemplated. According to one aspect, the nail includes an elongate member having a longitudinal axis, a proximal end section, and a distal end section and a central solid section extending therebetween. The proximal end section includes a fastener receiving portion enlarged relative to the central section and having at least one hole extending therethrough normal to the longitudinal axis. The distal end section includes a fastener receiving portion enlarged relative to the central section.

In one form, the distal fastener receiving portion includes a first hole therethrough normal to the longitudinal axis and a second hole therethrough normal to the longitudinal axis and normal to the first hole. In another form, the distal fastener receiving portion includes a first upper hole therethrough normal to the longitudinal axis and a second lower hole therethrough normal to the longitudinal axis and parallel to the first hole. In yet another form, the distal fastener receiving portion includes at least one hole therethrough normal to the longitudinal axis, and there is at least one middle fastener receiving portion formed along the central solid section between the proximal end section and the distal end section. The middle fastener receiving portion is enlarged relative to the central solid section and has a hole therethrough normal to the longitudinal axis.

Referring now to FIGS. 10–12, there is illustrated another embodiment intramedullary nail 220. Nail 220 has structural features and properties that are similar to nail 20 described above; however, nail 220 includes a distal end that allows placement of additional fasteners to provide added stability. While nail 220 has a length that makes it particularly suited for femur 10 having supracondylar fracture or osteotomy 92, applications for other types of femoral fractures and osteotomies are also contemplated.

Nail 220 includes a central solid section 222 extending between a proximal end section 234 and a distal end section 232. Except as otherwise provided herein, nail 220 generally has the structural, dimensional and elastic properties discussed above with respect to nail 20. Nail 220 has two widened sections or fastener receiving areas 228, 230 in respective distal and proximal end sections 232, 234. Smooth gradual transitions are provided between central section 222 and the fastener receiving areas 228, 230. Distal fastener receiving area 228 is positioned adjacent to and in spaced relation from distal tip 226 with a distal taper therebetween. The proximal fastener receiving area 230 extends to proximal tip 242, and can include a tool attachment structure as described above with respect to nail 20. Nail 220 can be bent and installed into femur 10 in a manner similar to that described above with respect to nail 20.

Proximal fastener receiving area includes a generally cylindrical hole 252 extending generally normal to the central longitudinal axis 254. Proximal fastener 264 can be placed through hole 252. Distal fastener receiving area 228 includes a lower generally cylindrical hole 250 extending normal to central axis 254, and an upper generally cylindrical hole 251 extending normal to axis 254 and also generally normal to hole 250, as shown in FIGS. 11 and 12. Upper distal fastener 260 can be placed through upper hole 251 and lower distal fastener 262 can be placed through lower hole 250, providing added stability when distal end portion 232 of nail 220 is secured to femur 10.

Figure 13:
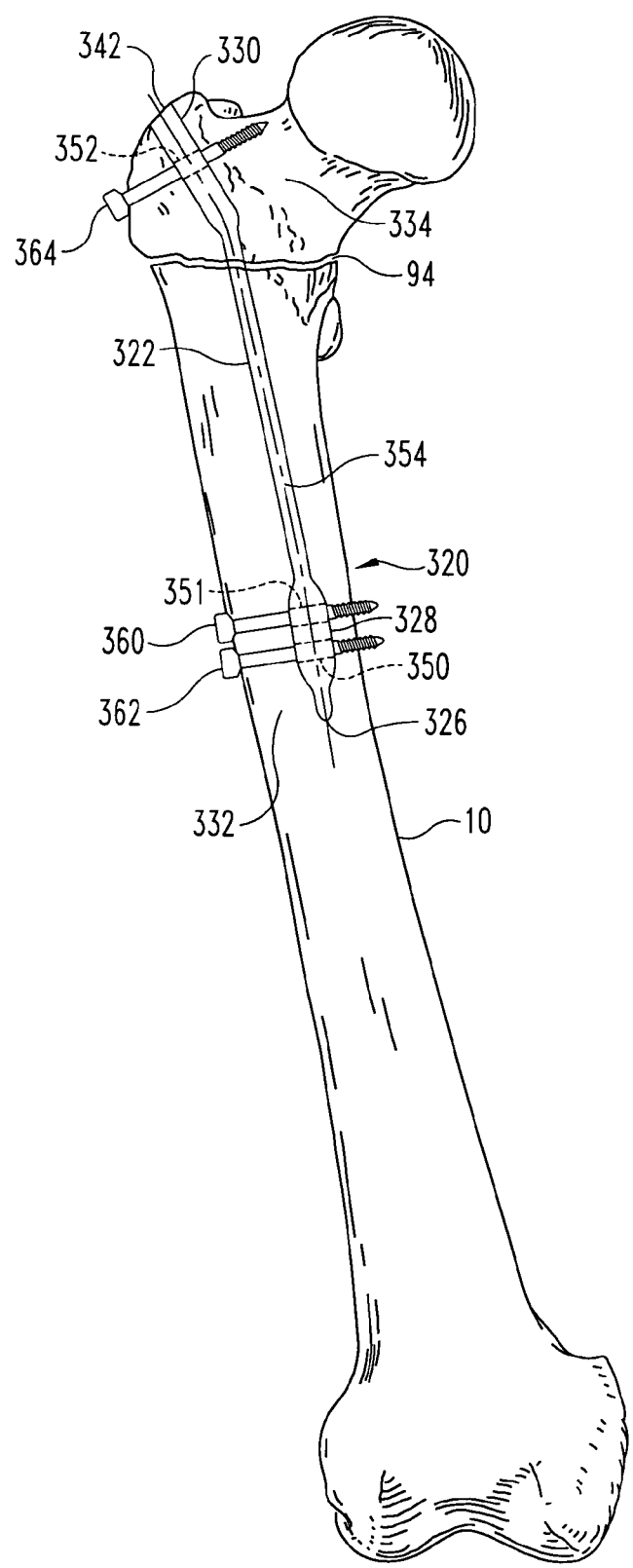
FIG. 13 is an elevational schematic view of a further embodiment bone nail according to the present invention fully inserted in the femur.

Referring now to FIG. 13, there is illustrated another embodiment bone nail 320 according to the present invention. Nail 320 preferably has a length that is particularly suited for a femur having an intertrochanteric osteotomy 94, which allows de-rotation of a twisted femur. Nail 320 has an enlarged distal fastener portion for receiving multiple fasteners therethrough. It is also contemplated that nail 320 also has application with other types of femoral fractures and osteotomies.

Nail 320 includes a central solid section 322, a proximal end section 334 and a distal end section 332. Except as otherwise provided herein, nail 320 generally has the structural, dimensional and elastic properties discussed above with respect to nail 20. Nail 320 has two widened sections or fastener receiving areas 328, 330 in respective distal and proximal end sections 332, 334. Smooth gradual transitions are provided between central section 322 and the fastener receiving areas 328, 330. Distal fastener receiving area 328 is positioned adjacent to and in spaced relation from distal tip 326 with a distal taper therebetween. The proximal fastener receiving area 330 extends to proximal tip 342, and can include a tool attachment structure as described above with respect to nail 20. Nail 320 can be bent and installed in a manner similar to that described above with respect to nail 20.

Proximal fastener receiving area includes a generally cylindrical hole 352 extending generally normal to the central longitudinal axis 354. Proximal fastener 364 can be placed through hole 352. Distal fastener receiving area 328 includes a lower generally cylindrical hole 350 extending normal to central axis 354, and an upper generally cylindrical hole 351 extending normal to axis 354 and also generally parallel to hole 350. Upper distal fastener 360 can be placed through upper hole 351 and lower distal fastener 362 can be placed through lower hole 350, providing added stability to distal end portion 332 of nail 320 secured to femur 10.

Figure 14:
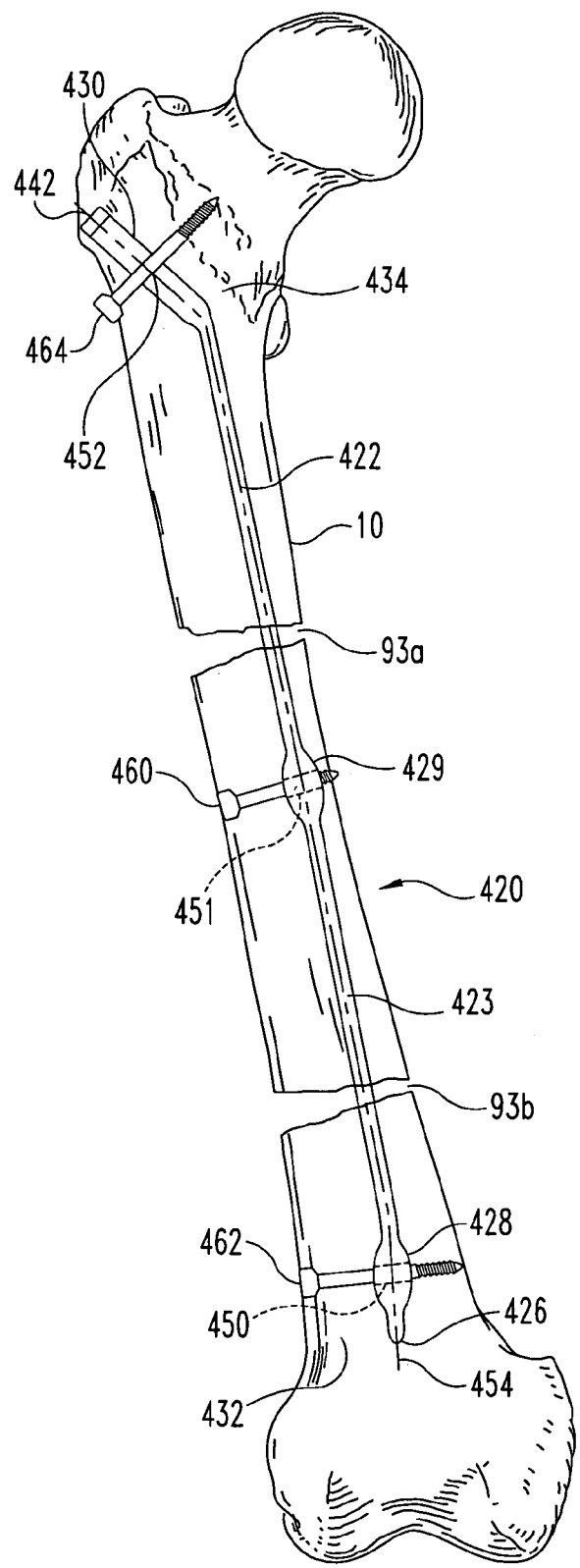
FIG. 14 is an elevational schematic view of yet another embodiment bone nail according to the present invention fully inserted in the femur.

Referring now to FIG. 14, there is illustrated another embodiment bone nail 420 according to the present invention. Nail 420 is particularly suited for multiple level osteotomies 93a, 93b for correction of femoral deformity, or for multiple fractures of the femur. It is also contemplated that nail 420 has application with other types of femoral fractures and osteotomies.

Nail 420 includes a pair of central solid sections 422, 423 extending from a middle fastener receiving section 429 towards a proximal end section 434 and a distal end section 432, respectively. Except as otherwise provided herein, nail 420 generally has the structural, dimensional and elastic properties discussed above with respect to nail 20. Nail 420 has widened sections or fastener receiving areas 428, 430 in respective distal and proximal end sections 432, 434. Nail 420 further has a middle widened fastener receiving area 429 between central sections 422, 423. Preferably, central sections 422, 423 have respective lengths that position middle receiving area 429 between upper osteotomy 93a and lower osteotomy 93b. Although the embodiment of FIG. 14 has one middle receiving area 429, it is contemplated that two or more middle receiving areas could be provided for use in multiple level fractures or osteotomies so that each section of bone has a fastener associated therewith. Smooth gradual transitions are provided between central section 422, 423 and the fastener receiving areas 428, 429, 430. Distal fastener receiving area 428 is positioned adjacent to and in spaced relation from distal tip 426 with a distal taper therebetween. The proximal fastener receiving area 430 extends to proximal tip 442, and can include an attachment structure as described above with respect to nail 20. Nail 420 can be bent and installed in a manner similar to that described above with respect to nail 20.

Proximal fastener receiving area 430 includes a generally cylindrical hole 452 extending generally normal to the central longitudinal axis 454. Proximal fastener 464 can be placed through hole 452. Distal fastener receiving area 428 includes a generally cylindrical hole 450 extending normal to central axis 454. Middle fastener receiving area 429 includes a generally cylindrical hole 451 extending normal to axis 254. Middle fastener 460 can be placed through hole 451 and distal fastener 462 can be placed through hole 450, securing nail 420 to each of the fractured sections of femur 10.

It may be appreciated by one skilled in the art that additional embodiments may be contemplated, including combinations of the above described embodiments. For example, the dual hole distal end portion of nail 220, 320 could be used with nail 20 or nail 420. It is also contemplated that additional embodiment may be similarly designed for nails used to fix fractures in long bones other than the femur in child and adolescent patients. It is also contemplated that similar nails could be used in repair of animal long-bone fractures.

In the foregoing description, certain terms have been used for brevity, clarity and understanding, but no unnecessary limitations are to be implied therefrom beyond the requirements of the prior art, because such words are used for description purposes herein and are intended to be broadly construed. Moreover, the embodiment of the apparatus illustrated and described herein are by way of example, and the scope of the invention is not limited to the exact details of construction illustrated herein.

While the invention has been illustrated and described in detail in the drawings and foregoing description, the same is to be considered as illustrative and not restrictive in character, it being understood that only the preferred embodiments have been shown and described and that all changes and modifications the come within the spirit of the invention are desired to be protected.

What is claimed is:

1. An intramedullary nailing system for fixing a fracture in a long bone of a patient having an intramedullary canal, the system comprising:
   an elongate member having a longitudinal axis, a proximal end section, a distal end section and a solid central section extending between said proximal and distal send sections, said proximal and distal end sections respectively including proximal and distal fastener receiving areas of greater cross-sectional dimensions than said central section, said fastener receiving areas each having at least one hole extending transverse to the longitudinal axis for receiving a cross fastener adapted to secure to the bone on opposite sides of said elongate member, said proximal and distal end sections thereby providing rigid anchoring locations relative to said central section, and said central section providing elastic flexibility to promote healing of the fracture, and
   a bending device having jaw structure configured to hold the elongate member and bend at least one of the proximal and distal end sections at relative to said central section.

2. The system of claim 1, wherein said bending device further comprises a pair of manually operable handles coupled with said jaw structure and adapted to be squeezed together to move the jaw structure.

3. The intramedullary nail of claim 1, wherein the ratio of the cross sectional dimensions of the respective proximal and distal fastener receiving areas at the axes of said holes relative to the cross sectional dimension of said central section is at least about 1.3:1.

4. The intramedullary nail of claim 1 further comprising cross fasteners respectively received in the holes, each cross fastener having a threaded distal tip, a threaded proximal shank and an unthreaded portion between the threaded distal tip and the threaded proximal shank, said unthreaded portion adapted to be received in one of said holes and said threaded distal tip and proximal shank adapted to engage bone matter on opposite sides of said one hole.

5. The intramedullary nail of claim 1, wherein said one of said fastener receiving areas included in said distal end section has at least two holes extending transverse to the longitudinal axis, said at least two holes each being normal to the longitudinal axis and one another.

6. The intramedullary nail of claim 1, wherein said nail is made from titanium and the nail has a generally cylindrical shape with a diameter of the solid central section of between about 4 and 7 millimeters.

7. The intramedullary nail of claim 1, wherein the central section has a solid cross section with a substantially constant diameter.

8. A method of fixing a fracture in a long bone of a patient having an intramedullary canal, the method comprising:
   providing a elongate member having a solid central section having a cross sectional dimension and having proximal and distal fastener receiving areas of increased cross sectional dimension relative to the cross sectional dimension of the central section, the fastener receiving areas each having at least one hole extending transverse to a longitudinal axis of the elongate member,
   inserting the elongate member into the intramedullary canal through an insertion point and across the fracture, and
   inserting cross fasteners through each of said holes and into said bone on opposite sides of said elongate member to fix the fracture of the long bone against rotational and lengthening movements.

9. The method of claim 8, wherein at least the central section of the elongate member is curved in a sagital plane of the patient, and further comprising:
   prior to the inserting step, laterally bending the proximal fastener receiving area of said elongate member at an acute angle out of the sagital plane of the patient.

10. The method of claim 9 further comprising:
    bending the distal fastener receiving area of said elongate member at an acute angle out of the sagital plane of the patient.

11. The method of claim 9 further comprising:
    laterally bending the proximal fastener receiving area to conform to a right femur of the patient.

12. The method of claim 9 further comprising:
    laterally bending the proximal fastener receiving area to conform to a left femur of the patient.

13. The method of claim 9, wherein the long bone in a femur and the insertion point is a point on the greater trochanter lateral of the piriformis fossa, and the method further comprises:
    laterally bending the proximal fastener receiving area to conform to the proximal femur of the patient and to present the proximal tip of the elongate member at the insertion point for access and removal after healing of the fracture.

14. The method of claim 8, which further includes providing another hole extending normal to the longitudinal axis of the elongate member and the at least one hole for at least one of the fastener receiving areas.

15. The method of claim 8, wherein the central section has a solid cross section with a substantially constant diameter.

* * * * *